United States Patent
Chiang et al.

(10) Patent No.: US 10,751,528 B2
(45) Date of Patent: Aug. 25, 2020

(54) IMPLANTABLE PULSE GENERATOR HEADERS INCLUDING CONNECTORS HAVING OFFSET SEGMENTS

(71) Applicant: PACESETTER, INC., Sylmar, CA (US)

(72) Inventors: Shichan Chiang, Valencia, CA (US); Evan Sheldon, Sherman Oaks, CA (US); Armando M. Cappa, Granada Hills, CA (US)

(73) Assignee: Pacesetter, Inc., Sylmar, CA (US)

(*) Notice: Subject to any disclaimer, the term of this patent is extended or adjusted under 35 U.S.C. 154(b) by 189 days.

(21) Appl. No.: 15/793,391

(22) Filed: Oct. 25, 2017

(65) Prior Publication Data

US 2019/0117962 A1  Apr. 25, 2019

(51) Int. Cl.
*A61N 1/05* (2006.01)
*A61N 1/375* (2006.01)
*A61N 1/04* (2006.01)
*A61N 1/39* (2006.01)

(52) U.S. Cl.
CPC ......... *A61N 1/0563* (2013.01); *A61N 1/3752* (2013.01); *A61N 1/37512* (2017.08); *A61N 1/0424* (2013.01); *A61N 1/3956* (2013.01); *A61N 1/3968* (2013.01)

(58) Field of Classification Search
USPC .................................................. 607/37, 119
See application file for complete search history.

(56) References Cited

U.S. PATENT DOCUMENTS

| | | | |
|---|---|---|---|
| 2004/0215280 A1* | 10/2004 | Dublin | A61N 1/37229 607/36 |
| 2008/0183235 A1* | 7/2008 | Stancer | A61N 1/375 607/36 |
| 2012/0245664 A1 | 9/2012 | Smith et al. | |

FOREIGN PATENT DOCUMENTS

| | | |
|---|---|---|
| EP | 2620180 A1 | 7/2013 |
| EP | 2620180 B1 | 5/2016 |
| WO | 2012/091987 A2 | 7/2012 |
| WO | 2012091987 A2 | 7/2012 |

OTHER PUBLICATIONS

Extended EP Search Report dated Feb. 26, 2019—Counterpart EP Pat. App. 18209359.1.
European Search Report, EP18205383.5, dated Apr. 18, 2019.

\* cited by examiner

*Primary Examiner* — Nicole F Lavert
(74) *Attorney, Agent, or Firm* — Polsinelli PC

(57) ABSTRACT

Disclosed herein is an implantable electronic device for use with an implantable medical lead. The implantable electronic device includes a housing and a header connector assembly coupled to the housing and adapted to receive the proximal lead end of the implantable medical lead. The header connector assembly includes a connector assembly including a connector, a feedthru extending through the housing, and a conductor coupling the feedthru to the connector. The conductor includes a first conductor segment and a second conductor segment offset from the first conductor segment and each of the first conductor segment and the second conductor segment are resistance welded to the connector.

18 Claims, 11 Drawing Sheets

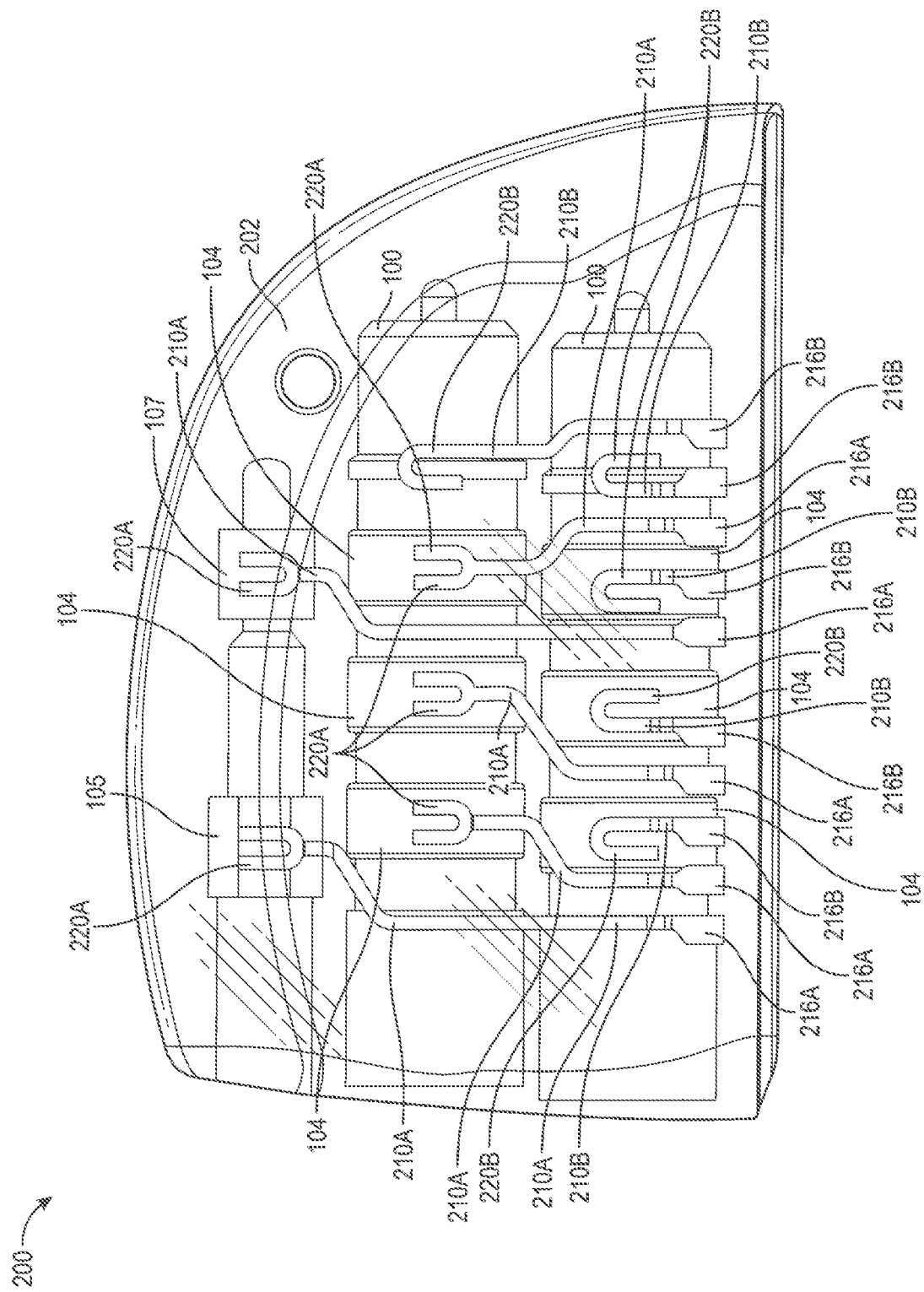

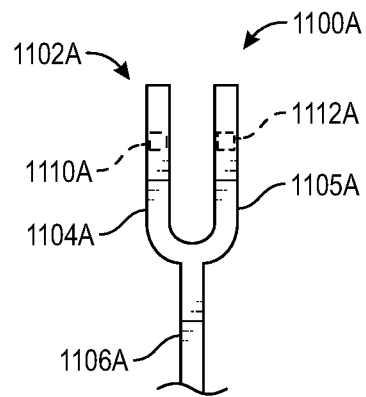
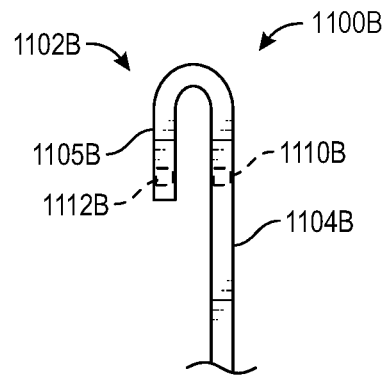
FIG. 11A  FIG. 11B
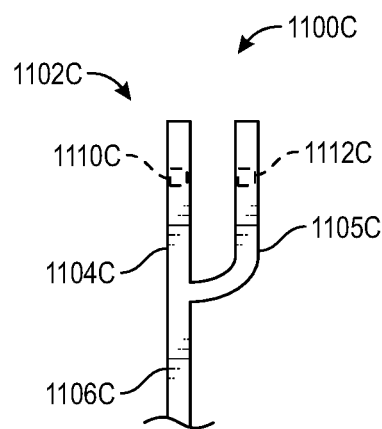
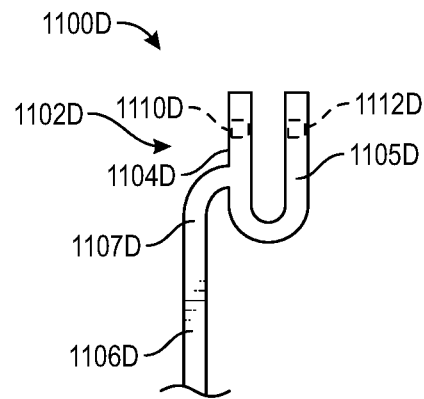
FIG. 11C  FIG. 11D

IMPLANTABLE PULSE GENERATOR HEADERS INCLUDING CONNECTORS HAVING OFFSET SEGMENTS

TECHNICAL FIELD

Aspects of the present disclosure relate to medical apparatus and methods. More specifically, the present disclosure relates to connector assemblies for use in a header of an implantable pulse generator.

BACKGROUND

Implantable pulse generators (IPGs) such as pacemakers and implantable cardioverter defibrillators (ICDs), which are used in the treatment of cardiac conditions, and neuromodulators or neurostimulators, which are used in chronic pain management or the actuation and control of other body systems, commonly include a housing, feedthrus, and a connector assembly that is enclosed in a header.

The connector assembly generally includes a bore into which an implantable medical lead may be inserted. Along the bore may be disposed one or more ring connectors positioned to contact corresponding ring terminals of a proximal end of the implantable medical lead when the proximal end is inserted into the connector assembly. The ring connectors are electrically coupled to the feedthrus, which in turn are electrically coupled to electrical components within the housing. Such electrical components may control, among other things, sensing, pacing, and defibrillation performed by the IPG.

Because the ring connectors form the primary means of sending and receiving electrical signals to the implantable medical leads, the connection between a given ring connector and its corresponding feedthru is critical to reliable operation of the IPG. Conventional methods in which a ribbon is resistance welded between a ring connector and its corresponding feedthru are prone to weld defects that undermine the strength and reliability of the ring connector-to-feedthru connection and, ultimately, the IPG as a whole.

Accordingly, there is a need in the art for systems and methods that improve the strength and reliability of the electrical connection between the ring connectors and their corresponding feedthrus by reducing the likelihood of weld defects.

BRIEF SUMMARY

In one embodiment of the present disclosure, an implantable electronic device for use with an implantable medical lead is provided. The implantable electronic device includes a housing, a feedthru extending through the housing, and a header assembly coupled to the housing and adapted to receive a proximal lead end of the implantable medical lead. The header assembly includes a connector assembly including a connector and a conductor coupling the feedthru to the connector. The conductor includes a first conductor segment and a second conductor segment offset from the first conductor segment, each of the first conductor segment and the second conductor segment being resistance welded to the connector.

In certain implementations, the conductor may be one of a ribbon conductor, a plate, and a wire. The first conductor segment and the second conductor segment may also be designed to provide substantially equal resistances during resistance welding.

In one implementation, the connector is a ring connector. In such an implementation, the first conductor segment and the second conductor segment may be curved to conform to a profile of the ring connector. In other implementations, the first conductor segment and the second conductor segment may be substantially flat. In another implementation, the conductor is formed from titanium and has a thickness from and including 0.003 inches to and including 0.050 inches.

The conductor may include a forked terminal portion including the first conductor segment and the second conductor segment such that the first conductor segment and the second conductor segment extending parallel to each other.

The conductor may also include a common segment such that the first conductor segment and the second conductor form a junction at the common segment. In such implementations, the common segment may have a width and each of the first conductor segment and the second conductor segment may be welded at a location a distance greater than or equal to the common segment width from the junction. In another implementation, the first conductor segment may be aligned with the common segment and the second conductor segment may extend from an offshoot of the common segment to extend parallel to the first conductor segment.

In another embodiment of the present disclosure, an implantable electronic device is provided that includes a connector and a conductor coupled to the connector. The conductor includes a first conductor segment and a second conductor segment offset from the first conductor segment and each of the first conductor segment and the second conductor segment are resistance welded to the connector.

In certain implementations, the conductor may be one of a ribbon conductor, a plate, and a wire. The first conductor segment and the second conductor segment may also be designed to provide substantially equal resistances during resistance welding. The conductor may be formed from titanium and may have a thickness from and including 0.003 inches to and including 0.050 inches.

In implementations of the present disclosure, the connector may be a ring connector. The conductor may include a forked terminal portion including the first conductor segment and the second conductor segment such that the first conductor segment and the second conductor segment extending parallel to each other.

In another embodiment of the present disclosure, a method of manufacturing an implantable electronic device is provided. The method includes abutting a conductor against a connector where such abutting includes abutting each of a first conductor segment of the conductor and a second conductor segment of the conductor offset from the first conductor segment against the connector. The first conductor segment is then contacted with a first electrode and the second conductor segment is contacted with a second electrode. The first conductor segment and the second conductor segment are then resistance welded to the connector by passing a current between the first electrode and the second electrode.

In one implementation, the connector is a ring connector and the method further includes conforming each of the first conductor segment and the second conductor segment to a curved surface of the ring connector.

In another implementation, the first conductor segment and the second conductor segment form a junction at a common conductor segment having a common segment width. In such implementations, contacting the first conductor segment with the first electrode and the second conductor segment with the second electrode includes contacting each of the first conductor segment and the second conductor segment at a location a distance greater than or equal to the common segment width from the junction.

While multiple embodiments are disclosed, still other embodiments of the present disclosure will become apparent to those skilled in the art from the following detailed description, which shows and describes illustrative embodiments of the disclosure. As will be realized, the various embodiments in this disclosure are capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

FIGS. 7A-7B are isometric and side views, respectively, of a header connector assembly according to the present disclosure.

FIGS. 11A-G are schematic illustrations of example ribbon conductors in accordance with the present disclosure.

DETAILED DESCRIPTION

Figure 1:
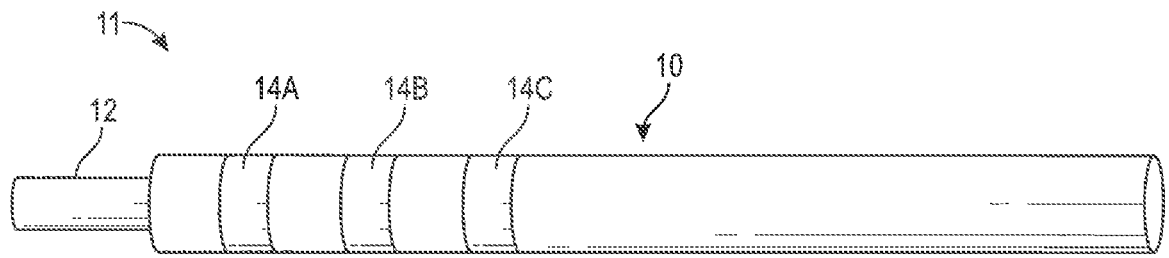
FIG. 1 is an isometric view of a proximal end portion (i.e., lead connector end) of a conventional quadripolar pacing lead conforming to the IS-4/DF-4 standards.

Implementations of the present disclosure involve an implantable electronic device, such as an implantable pulse generator (IPG), that may be used, for example, to administer electrotherapy or other neurostimulation via an implantable lead having a lead connector end on a proximal end of the implantable lead. The IPG includes a housing or can and a connector assembly enclosed in a header, both of which are coupled to the housing or can. The header includes one or more connector assemblies. Each connector assembly includes a lead connector receiving bore or receptacle that includes electrical contacts that make electrical contact with corresponding electrical terminals on the lead connector end on the proximal end of the implantable lead when the lead connector end is plugged into or otherwise received in the lead connector receiving bore or receptacle. Via the electrical connection between the corresponding electrical terminals of the lead connector end and the electrical contacts of the lead connector receiving bore, electrical signals can be administered from the IPG and through the lead to patient tissue. Similarly, but in reverse, electrical signals originating in patient tissue can travel via the lead to the IPG to be sensed at the IPG.

The electrical contacts of the connector assembly may include circular ring electrodes. The circular ring electrodes are in turn coupled to feedthrus that extend into the housing or can by a ribbon or similar conductor. Conventionally, each ribbon conductor is a single strip of conductive material that may be resistance welded to a ring electrode and welded or otherwise electrically coupled to a corresponding feedthru.

Resistance welding is a joining process in which workpieces to be welded are disposed between two electrodes, forming an electrical loop. A controlled electric current is then passed between the electrodes through the workpieces. Because of resistance to current flow, the elements in the electrical loop heat up. While the electric heating occurs on all dements in the electric loop, a majority of heat is generated at the interface of the workpieces which generally has a higher resistance than other elements defining the electric loop. Localized heating at the interface softens and melts the material of the workpieces adjacent the interface. This melting combined with pressure applied by the electrodes forms a weld between the workpieces.

In opposed welding, the electrodes used to resistance weld the two workpieces are disposed on opposite sides of the workpieces. In contrast, parallel gap welding involves side-by-side placement of the electrodes such that a first electrode is made to contact a first workpiece placed onto a second workpiece while a second electrode is made to contact the second workpiece directly at a predetermined distance from the first electrode. When current is subsequently passed between the electrodes, the current travels through each of the first and second workpieces, forming a weld at the interface of the first and second workpieces.

Conventional parallel gap welding has been used to weld ribbon conductors to connectors of IPG connector assemblies. In such implementations, a ribbon conductor is placed onto a connector, such as a ring connector. A first electrode is then placed onto the ribbon conductor while a second electrode is placed onto the connector. Current is then passed between the electrodes, welding the ribbon conductor to the connector. However, the conventional approach to resistance welding ribbon conductors to connector assembly connectors can lead to significant issues regarding weld quality and weld strength, particularly when trying to weld a fiat ribbon connector to a curved component such as a ring connector. More specifically, parallel gap welding may lead to significant indentation and scarring on both the ribbon conductor and the connector at the electrode locations, in addition to being unsightly, such damage can impact the durability of the ribbon conductor and connector and the quality of the electrical connection formed between the ribbon conductor and the connector.

Weld defects on the connector side may arise due to the relatively limited contact area between the electrode and the connector. In many parallel gap welding applications, the electrodes have faces that are flat such that when abutted against a curved surface, a line contact occurs between the electrode and the ring connector. When current is then passed to or from the electrode, the current is concentrated in a limited area of the ring connector, rapidly heating the interface between the electrode and the ring connector. Such rapid heating may lead to, among other things, excessive melting, weld spatters, and blown molten metal, each of which may form a weld scar at the interface of the electrode and the ring connector.

In addition to causing weld defects on the connector side, the limited contact area between the electrode and the connector triggers instability in the current (and, as a result, the heat) delivered through the electrical loop, which in turn impacts the stability of current provided to the interface between the ribbon conductor and the connector.

Weld defects on the ribbon conductor side may similarly be caused by limited contact area between the ribbon conductor and the underlying connector. More specifically, in instances where a flat ribbon conductor is welded to a curved connector, such as a ring connector, the ribbon conductor is substantially tangential to the connector and, as a result, current passed between the electrodes becomes concentrated at the interface of the ribbon conductor and connector. This instability may lead to, among other things, an inconsistent depression formed on the ribbon conductor which may impact to the overall integrity of the weld formed between the ribbon conductor and the connector.

Additionally, the compressive force applied by the electrode to the ribbon conductor during welding may cause deformation of the ribbon conductor, thereby increasing the contact area between the ribbon conductor and the underlying connector. By doing so, the electrical resistance at the interface between the ribbon conductor and the connector may be reduced, limiting the weld heat generation and causing lower or inconsistent weld strength. In other words, the conventional parallel gap welding setup, particularly in instances where a flat conductor ribbon is welded to a curved connector, creates a condition of "unbalanced" interface resistance which induces weld defects and poor weld integrity.

To overcome the foregoing issues, among others, connector assemblies and IPGs in accordance with this disclosure include ribbon conductors having offset segments. In one implementation, for example, the ribbon conductor includes a common segment that terminates in a forked end having parallel offset segments. During manufacturing of a connector assembly in accordance with this disclosure, each of the offset segments of the ribbon conductor are placed onto the connector and respective electrodes of a resistance welding system are made to contact and apply pressure to each of the offset segments. As a result, each of the electrodes has a substantially similar interface such that the resistance at the first electrode and the second electrode is substantially balanced. This reduces high current concentrations and imbalances that may lead to excessive heating, spatter, and other causes of defective welds. As further described herein, the use of ribbon conductors having offset segments may be applied in instances in which a flat ribbon conductor is welded to either a flat or curved connector and also when a curved ribbon conductor is welded to a curved connector, in experimental use, ribbon conductors in accordance with this disclosure demonstrated improved weld appearance (surface quality), weld strength, and weld consistency as compared to conventional parallel gap welding of single strand ribbon conductors.

Although the implementations described herein are primarily described as including ribbon conductors, other conductors may be used to couple connectors to corresponding feedthrus. Accordingly, implementations of the present disclosure are not limited to including ribbon conductors and other types of conductors having offset segments may also be used. Such conductors may include, without limitation, plates and wires.

Before beginning a detailed discussion of ribbon conductors and connector assemblies suitable in accordance with this disclosure and for use in IPG headers, a general discussion is first given regarding features of a common lead connector end. A subsequent general discussion describes the features of conventional IPGs and header assemblies.

FIG. 1 shows a proximal end portion 10 of a conventional transvenous, quadripolar or IS-4 type pacing lead, but is generally representative of any type of implantable lead whether in the cardiac, pain management or other medical treatment space. The diameter of such a lead may be made a sufficiently small diameter to facilitate the lead's implantation into small veins such as those found in the coronary sinus region of the heart and to allow implantation of a plurality of leads into a single vessel for multi-site or multi-chamber pacing. While the lead whose proximal end is shown in FIG. 1 is of the quadripolar or IS-4 variety, there are other leads with a different number of electrodes that may be generally represented by the lead in FIG. 1.

As is well known in the art, IS-4/DF-4 leads typically consists of a tubular housing of a biocompatible, biostable insulating material containing four conductor coils each surrounded by an insulating tube. One of the conductor cons is connected to a tip electrode at an end of the lead. The remaining three conductor coils are connected to annular ring electrodes, spaced-apart from each other, along the end portion of the lead. The four conductor cons are insulated from each other to electrically isolate the cons and, thus, prevent any internal electrical short circuit, while the housing protects the entire lead from the intrusion of body fluids. These insulating materials are typically either silicone rubber or polyurethane.

As seen in FIG. 1, the proximal lead end portion 10 includes a lead connector end 11 that conforms to the IS-4/DF-4 standard, including three spaced-apart electrical ring terminals 14A-14C and a tip terminal 12. Ring terminal 14A corresponds to the ventricular pace sense ring connection, ring terminal 14B corresponds to the right ventricle or RV coil connection, and ring terminal 14C corresponds to the superior vena cava or SVC coil connection. The tip terminal 12 corresponds to the ventricular pace sense tip electrode connection. The tip terminal 12 is electrically connected by means of one of the inner conductor coils to the tip electrode at the distal end of the lead. The ring terminals 14A-14C are electrically connected to the three conductor cons contained within the tubular housing.

Figure 2:
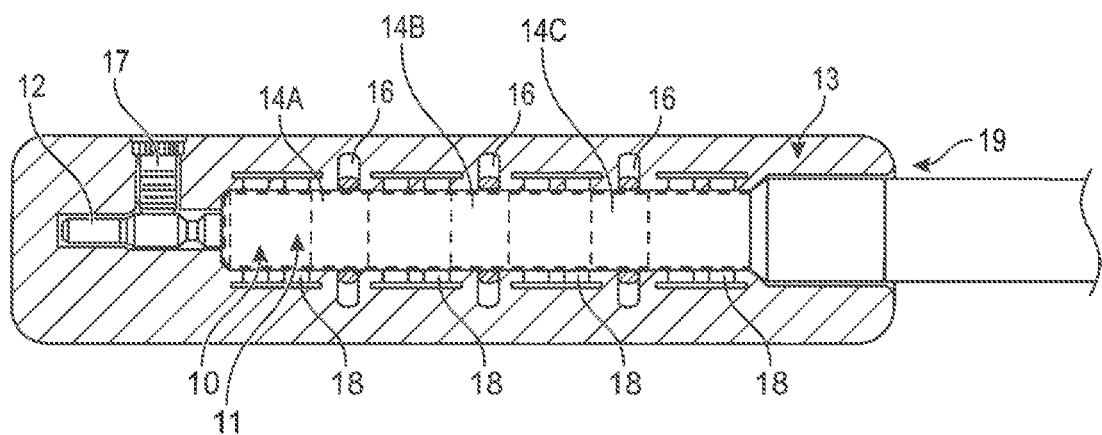
FIG. 2 is a side view of the proximal lead end portion of a lead positioned within a conventional connector assembly conforming to the IS-4/DF-4-standards.

As seen in FIG. 2, which is a side view of the proximal lead end portion 10 positioned within a conventional connector assembly 13 conforming to the IS-4/DF-4 standards, the ring terminals 14A-14C of the lead connector end 11 may each be engaged by a conductive garter spring contact 16 or other resilient electrical contact element in a corresponding lead connector receiving bore of the header, the resilient electrical contact element being carried by the connector assembly 13 enclosed in the header as described below. The tip terminal 12 may be engaged by a conductive set screw 17.

The connector assembly 13 further includes spaced-apart seal rings 18 for abutting against in a fluid-sealing and electrically insulating manner the outer circumferential surface of the lead connector, thereby preventing body fluids from reaching the electrical terminals and contacts when the lead connector end 11 is plugged into the bore 19 of the connector assembly 13. With the lead connector end 11 of the lead inserted in the bore 19 of the connector assembly 13, the tip terminal 12 and ring terminals 14A-14C are electrically coupled via the contacts 16, 17 of the connector assembly 13 and a feedthru to the electronic circuits within the hermetically sealed housing of the IPG (e.g., cardiac pacemaker, ICD, or other implantable tissue stimulation and/or sensing device such as those used in pain management, etc.).

Figure 3:
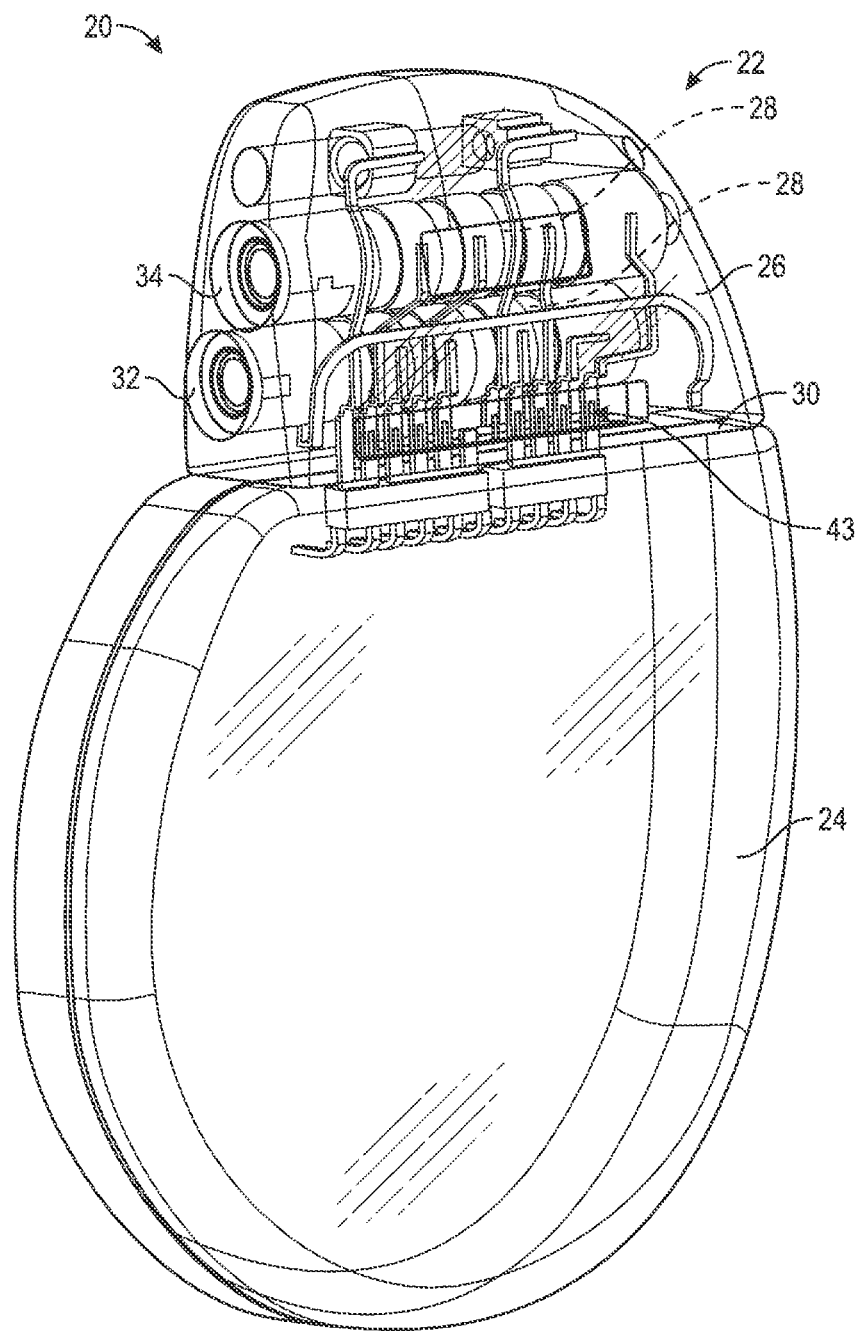
FIG. 3 is an isometric view of a conventional cardiac pacemaker/defibrillator unit (i.e., implantable pulse generator (IPG)) having a header connector assembly and a housing.

FIG. 3 shows an isometric view of a cardiac pacemaker/defibrillator unit that is generally representative of any type of IPG 20 incorporating a header connector assembly 22 coupled to a housing 24. The header connector assembly 22 includes a header 26 enclosing a pair of connector assemblies 28. While the header connector assembly 22 shown in FIG. 3 depicts two connector assemblies 28, the header may include more or fewer connector assemblies 28 without departing from the teachings of the present disclosure. The IPG 20 includes a hermetically sealed housing 24, which is also known as a can or casing. The housing 24 encloses the electronic components of the IPG 20 with the header connector assembly 22 mounted along a top edge 30 of the housing 24.

As shown in FIG. 3, the header 26 may include two connector assembly receiving bores or receptacles 32, 34 for receiving the connector assemblies 28, which then receive the lead connector ends of two implantable leads. Other headers 26 may include more or fewer connector receiving bores 32, 34 as required by the particular IPG 20 requirements. For example, a particular IPG 20 utilizing a high voltage DF-4 connector may only require a single connector assembly receiving bore 32.

Figure 4:
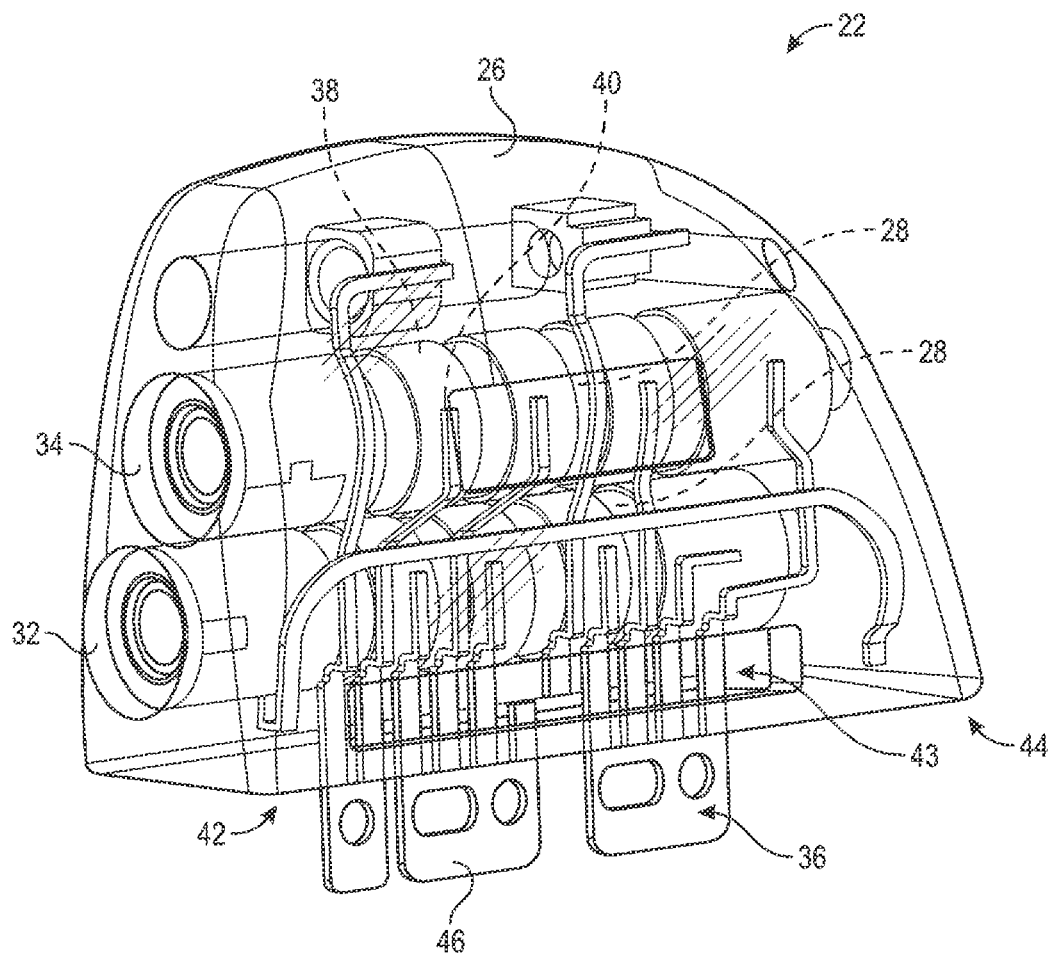
FIG. 4 is an isometric close-up view of the header connector assembly of FIG. 3

FIG. 4 is an isometric close-up view of the header 26 of FIG. 3. As seen in the figure, an electrical connection assembly 36 electrically connects between ring connectors 38 of the connection assemblies 28 and the electrical componentry in the housing 24 (not shown in FIG. 4). More particularly, the electrical connection assembly 36 includes individual ribbon conductors 40 that contact (e.g., weld) the ring connectors 38 of the connection assemblies 28 and extend to corresponding feedthrus 43 of the electrical connection assembly 36. The feedthrus 43 of the electrical connection assembly 36 extend between the connector assemblies 28 and the can 24. As seen in FIG. 4, the header 26 includes an opening 42 on a bottom side 44 of the header 26 for the lower end 46 of the electrical connection assembly 36 to extend into the housing 24. As previously noted, the housing 24 is hermetically sealed and, as a result, the feedthrus 43 generally extend into the housing 24 in a manner that maintains the hermetic seal of the housing 24.

Figure 5:
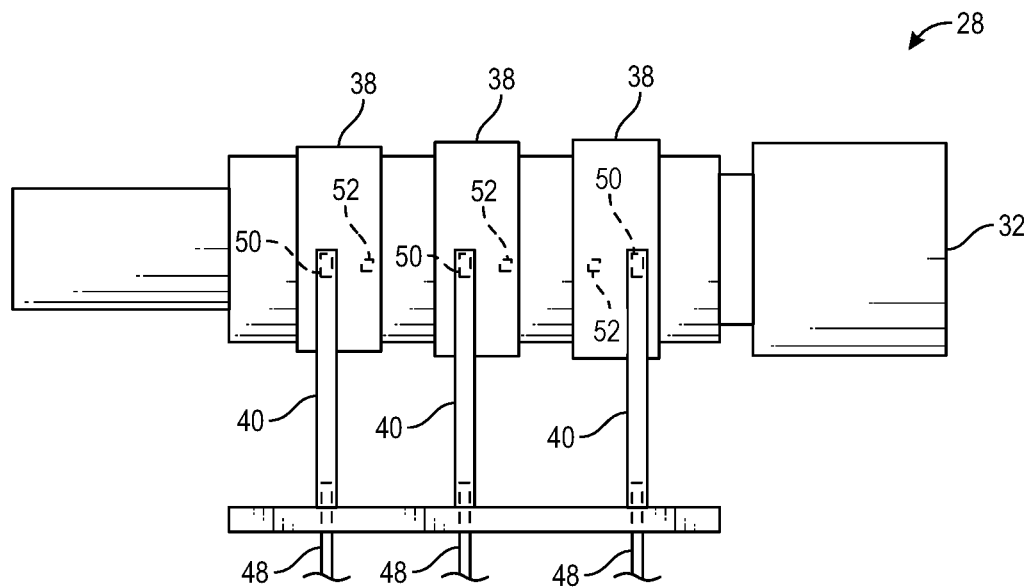
FIG. 5 is a side view of a conventional connector assembly.

FIG. 5 is a side view of a conventional connection assembly 28. As previously discussed, the connection assembly 28 generally includes a receptacle 32 into which a proximal end of an implantable lead may be inserted. The connection assembly 28 further includes one or more ring connectors 38 which are coupled to corresponding feedthrus 48 of an electrical connection assembly 36 (as shown in FIG. 4) by respective ribbon conductors 40.

As shown in FIG. 5, each of the ribbon conductors 40 is welded to a corresponding ring connector 38. Welding of the ribbon conductors 40 to the ring connectors 38 may be accomplished using parallel gap resistance welding. To do so, each ribbon conductor 40 is positioned on its respective ring connector 38. Electrodes are then placed on the ribbon conductor 40 and the ring connector 38. More specifically, a first electrode (not shown) is disposed at a first electrode location 50 such that the first electrode contacts and maintains pressure on the ribbon conductor 40 and a second electrode (not shown) is disposed at a second electrode location 52 such that the second electrode contacts and maintains pressure on the ring connector 38. A current is then passed between the first and second electrodes, causing heating at the interface between the ribbon conductor 40 and the ring connector 38, forming a melt pool at the interface that, when cooled, welds the ribbon conductor 40 to the ring connector 38.

Figure 6:
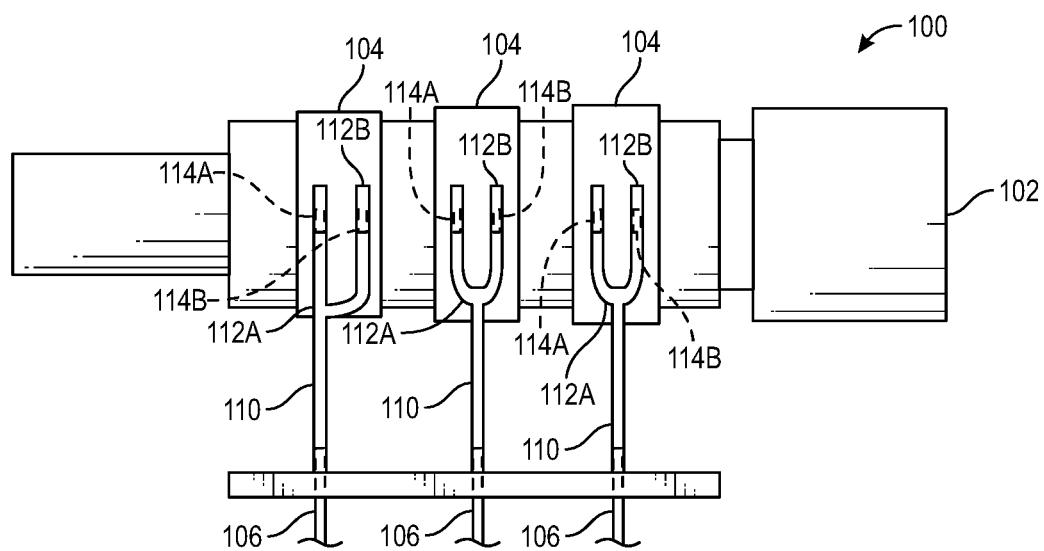
FIG. 6 is a side view of a header connector assembly according to the present disclosure.

FIG. 6 is a connection assembly 100 according to the present disclosure. The connection assembly 100 includes a receptacle 102 into which a proximal end of an implantable lead may be inserted. The connection assembly 100 further includes one or more ring connectors 104 which are coupled to corresponding feedthrus 106, each of which may extend and be combined in an electrical connection assembly, such as the electrical connection assembly 36 of FIG. 4. In contrast to the ribbon conductors 40 of FIG. 5, the connection assembly 100 includes forked ribbon conductors 110.

As shown in FIG. 6, each of the ribbon conductors 110 is welded to a corresponding ring connector 104 using a parallel gap resistance welding process. To do so, each ribbon conductor 110 is positioned on its respective ring connector 104. In contrast to the conventional connection assembly 28 illustrated in FIG. 5 in which one electrode contacts the ribbon conductor 50 and one electrode contacts the ring connector 38, each electrode in the example implementation of FIG. 6 contacts a portion of a ribbon conductor 110 and, more specifically, one of two offset segments 112A, 112B of the ribbon conductor 110. Each of the offset segments 112A, 112B of the, ribbon conductor 110 is formed to be substantially similar such that the resistance and contact area of each segment is similar. Accordingly, a first electrode (not shown) contacts and maintains pressure on a first segment 112A of the ribbon conductor 110 at a first electrode location 114A while a second electrode (not shown) contacts and maintains pressure on a second segment 112B of the ribbon conductor at a second electrode location 114B. A current is then passed between the first and second electrodes, causing heating at the interfaces between each of the first segment 112A and the second segment 112B and the ring connector 104, forming respective melt pools that, when cooled, weld each of the segments 112A, 112B to the ring connector 104.

By dividing each ribbon conductor 110 into separate, offset segments 112A, 112B and welding each of the offset segments 112A, 112B to a respective ring connector 104, the overall quality and strength of the connection between the ribbon conductors 110 and their respective ring connectors 104 is improved. When welding the ribbon conductor 50 to the ring connector 38 in the connector assembly 28 of FIG. 5, the contact area and resistance at each of the first and second electrodes varies. More specifically, the resistance and contact area of the first electrode, which contacts the ribbon conductor 50 is different than that of the second electrode, which contacts the ring connector 38 directly, in cases where a flat ribbon conductor and flat-faced electrodes are used, for example, the flat face of the first electrode will substantially abut the ribbon conductor 50 such that the contact area is essentially the entire face of the electrode; however, the second electrode will contact the ring connector 48 along a line due to the curvature of the ring connector 48. Moreover, the ribbon conductor 50 forms an area of increased resistance ribbon conductor 50 adjacent the first electrode. As a result of these imbalances in contact area and resistance, current concentrations may arise that cause uneven, localized heating within the ribbon conductor 50 and the ring connector 38 which may lead to weld defects. In contrast, the contact area and resistance at each of the first and second electrodes when welding the segments 112A, 112B of the ribbon conductors 110 to the ring connector 104

(as shown in FIG. 6) are substantially identical. As a result, the current concentrations and uneven heating of conventional methods of joining ribbon conductors to connectors are avoided, leading to improved weld quality and strength.

Figure 7A:
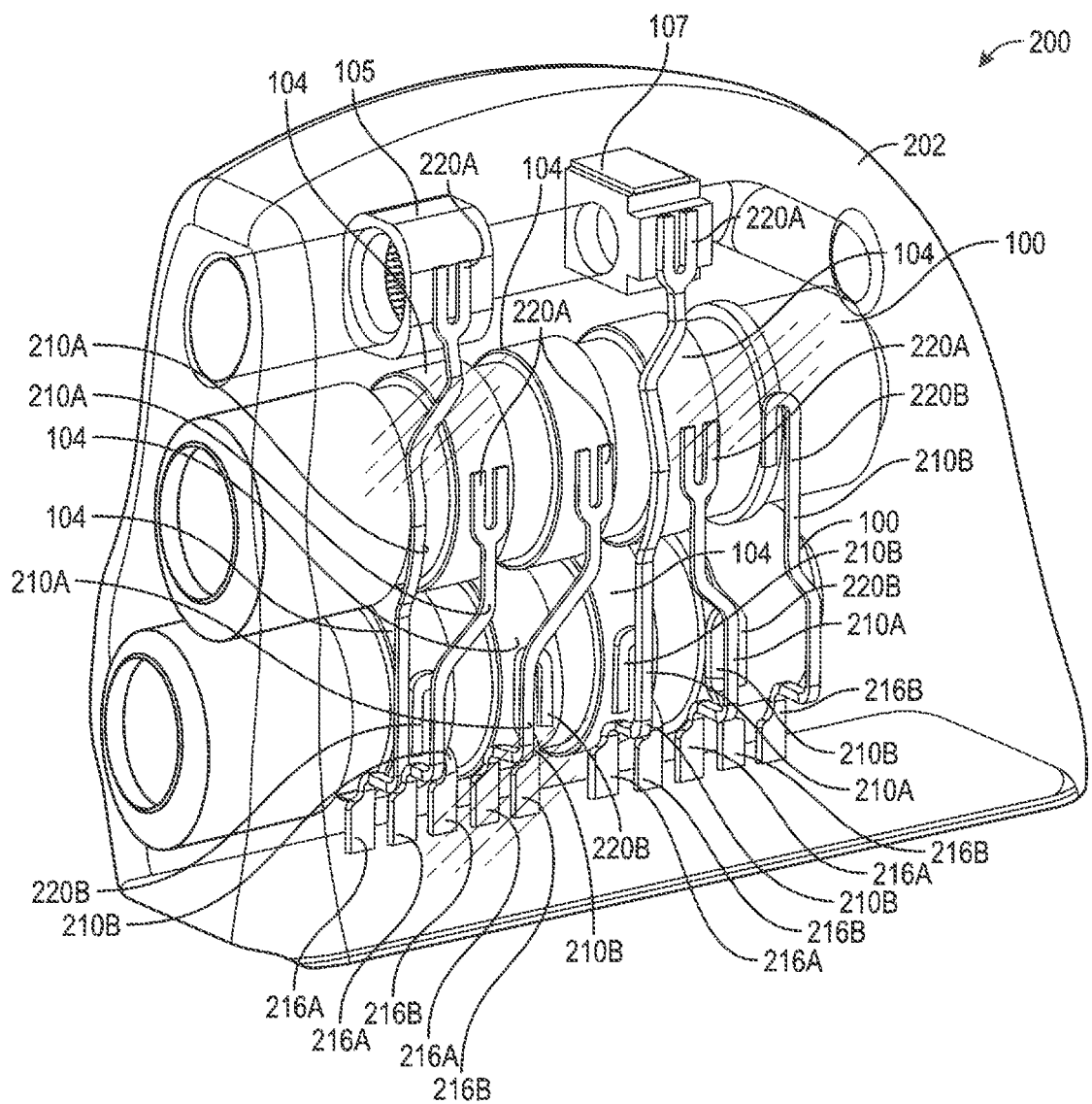

FIG. 7A is an isometric close-up view of a header 200 having a header body 202 that includes and supports electrical connection assemblies 100 having ribbon conductors 210A, 210B in accordance with the present disclosure. FIG. 7B is a side view of the header 200. The header 200 may be coupled to a housing or can, such as the housing 24 shown in FIG. 3. As seen in FIGS. 7A-7B, each connection assembly 100 includes ring connectors 104 coupled to ribbon conductors 210A, 210B. Each of the ribbon conductors 210A terminates in a forked terminal portion 220A including parallel segments which are individually welded to connectors, such as the ring connectors 104, a connector block 105, or a terminal conductor 107. Similarly, each of the ribbon conductors 210B terminates in a U-shaped terminal portion 220B including parallel segments which are individually welded to connectors. The ribbon conductors 210A, 210B further include tabs 216A, 216B disposed opposite each of the respective forked terminal portions 220A or U-shaped terminal portions 220B. Each tab 216A, 216B may in turn be coupled, such as by welding, to a corresponding feedthrough of the housing 106 (shown in FIG. 6) during assembly. As shown in FIGS. 7A-7B, each ribbon conductor 210A, 210B may vary in length and may include one or more bends such that the tabs 216A, 216B are disposed in predetermined locations within the header body 202.

Figure 8A:
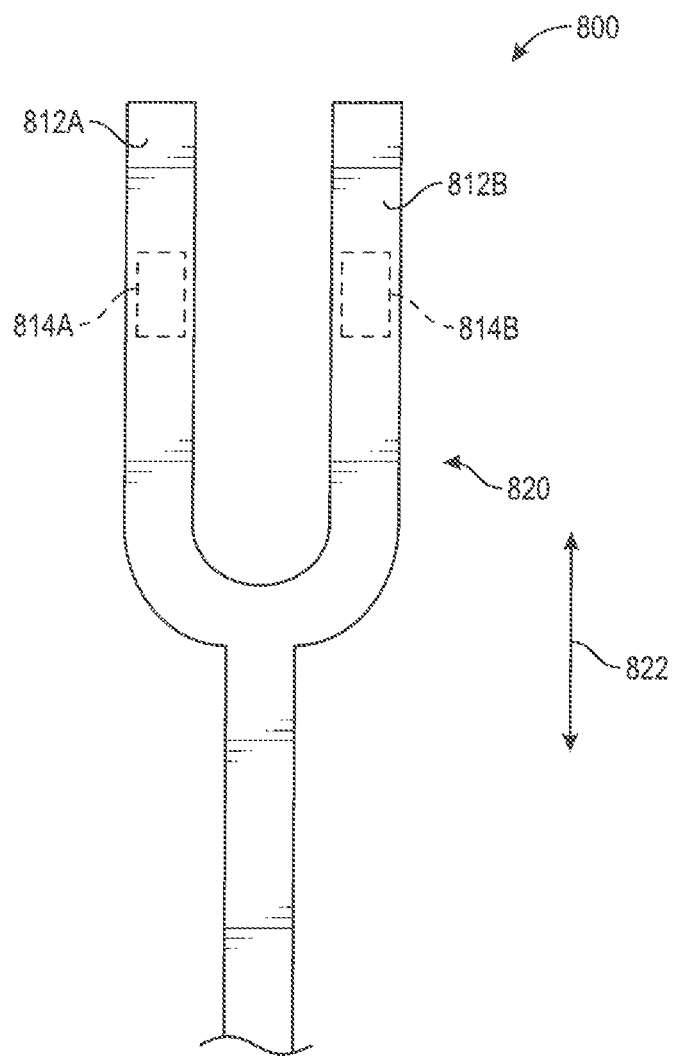
FIGS. 8A-8B are top plan and front views, respectively, of a forked ribbon conductor in accordance with the present disclosure.
Figure 8B:
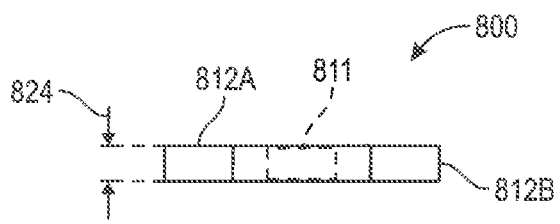

FIGS. 8A and 88 are top plan and front views of an example ribbon conductor 800 and, more specifically, a terminal portion 820 of the example ribbon conductor 800. The terminal portion 820 is shown as having a common segment 811 extending in a longitudinal direction 822 and that splits to form two parallel segments 812A, 812B that similarly extend in the longitudinal direction 822.

In certain implementations, predetermined weld locations 814A, 814B may be identified for each of the segments 812A, 812B. The predetermined weld locations 814A, 814B generally correspond to the locations at which electrodes are placed during welding of the ribbon conductor 800 to a connector, such as the ring connectors 104 shown in FIG. 6.

The ribbon conductor 800 is preferably formed of a biocompatible conductive material. For example, in certain implementations, the ribbon conductor 800 is formed from titanium. The ribbon conductor 800 may have a thickness 824 that varies between implementations of the present disclosure; however, in general, the thickness 824 of the ribbon conductor 800, and particularly the ribbon conductor segments 812A, 812B, is substantially uniform. In certain implementations, the thickness 824 of the ribbon conductor 800 is from and including 0.003 inches to and including 0.050 inches.

During the resistance welding process, current passed between the welding electrodes may be diverted to adjacent structures in what is commonly referred to as "shunting," For example, in applications in which spot welds are made in close proximity, a portion of the current passed between the welding electrodes may be diverted through a previously formed weld as opposed to passing directly between the electrodes.

In applications of the present disclosure, shunting may occur through the common segment 811. More specifically, as current is passed between the parallel segments 812A, 812B, a portion of the current may instead pass through the common segment 811. Such shunting may be minimized or even eliminated by sufficient spacing between the weld locations 814A, 814B and the common segment 811. In general, ensuring that the weld locations 814A, 814B are at least one ribbon width away from the common segment 811 avoids or sufficiently limits shunting through the common segment 811. So, for example, if the common segment 811 has a width of approximately 0.030 inches, the weld locations 814A, 814B should be disposed at least that distance from the common segment 811.

Figure 9A:
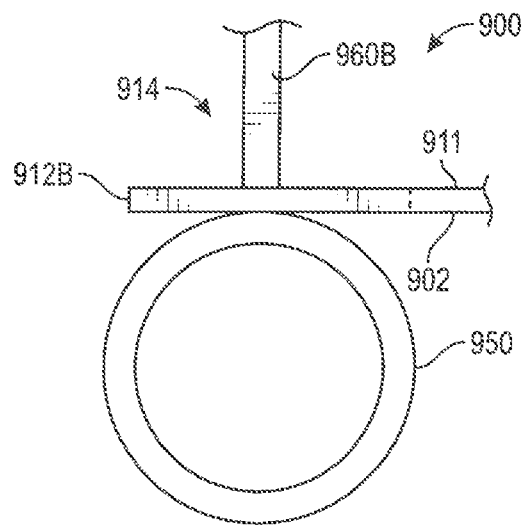
FIGS. 9A and 9B are side views of a first assembly including a ribbon conductor being coupled to a ring connector in a flat configuration.
Figure 9B:
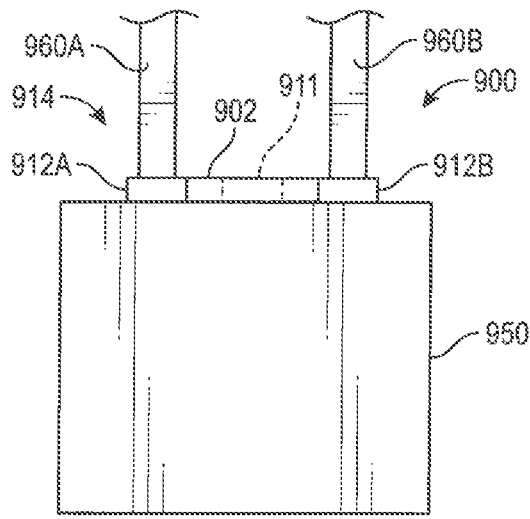

FIGS. 9A and 9B illustrate a first assembly 900 in which a ribbon conductor 902 is in the process of being welded to a ring connector 950. The ribbon conductor 902 is substantially flat and has a forked terminal end portion 914. The terminal end portion 914 includes a first segment 912A and a second segment 912B that extend parallel to each other and in-line with the terminal end portion 914 and that join at a common segment 911. As illustrated in FIG. 9B, during welding, a first electrode 960A is made to abut the first segment 912A and a second electrode 960B is made to abut the second segment 912B. The electrodes 960A, 960B may also apply pressure to their respective segments 912A, 912B to ensure contact between the segments 912A, 912B and the ring connector 950 during welding. Current may then be passed between the electrodes 960A, 960B to weld the segments 912A, 912B to the ring connector 950.

Figure 10A:
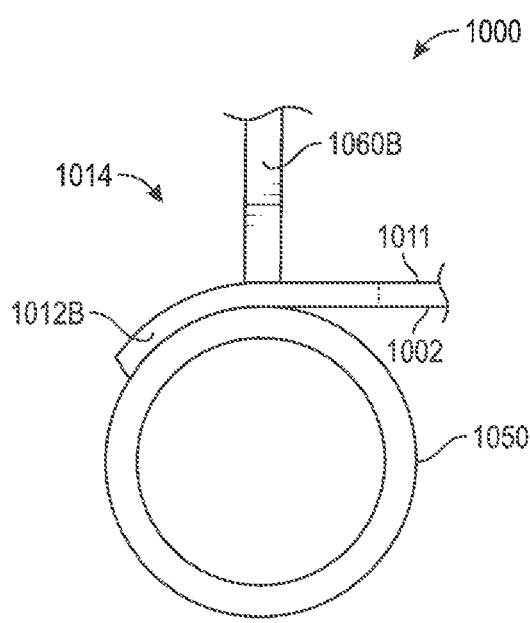
FIGS. 10A and 10B are side views of a second assembly including a ribbon conductor being coupled to a ring connector in a curved configuration.
Figure 10B:
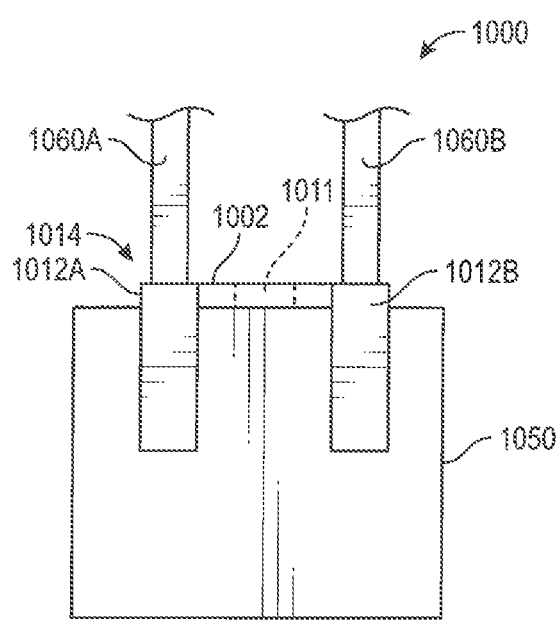

FIGS. 10A and 103 illustrate a second assembly 1000 in which a ribbon conductor 1002 is in the process of being welded to a ring connector 1050. The ribbon conductor 1002 is has a forked terminal end portion 1014 that further includes a first segment 1012A and a second segment 1012B that extend parallel to each other and join at a common segment 1011. In contrast to the flat segments 912A, 912B of FIGS. 9A and 96, the segments 1012A. 1012B of FIGS. 10A-10B are curved to conform to the surface of the ring connector 1050. In certain implementations, the segments 1012A, 1012B may be preformed to conform to the curvature of the ring connector 1050. In other implementations, the segments 1012A, 1012B may be flexible such that they may be bent to conform to the ring connector 1050 after placement of the segments 1012A, 1012B on the ring connector 1050. As illustrated in FIG. 106, during welding, a first electrode 1060A is made to abut the first segment 1012A and a second electrode 1060B is made to abut the second segment 1012B, each to the electrodes 1060A, 1060B also applying pressure to their respective segments 1012A, 1012B. Current may then be passed between the electrodes 1060A, 1060B to weld the segments 1012A, 1012B to the ring connector 1050.

The shape of ribbon conductors in accordance with the present disclosure may vary provided the ribbon conductors include segments corresponding to weld locations having substantially equal resistances, Accordingly, although previously described as having a forked shape, other shapes of ribbon conductors may be implemented that maintain balanced resistance between weld locations. FIGS. 11A-11G illustrate different examples of ribbon conductors in accordance with the present disclosure. The ribbon conductors of FIGS. 11A-11G are intended only as examples and other ribbon conductor shapes may be implemented in IPGs and connector assemblies in accordance with the present disclosure. Moreover, while illustrated in FIGS. 11A-11G as being substantially flat, any of the ribbon conductors of FIGS. 11A-11G may be curved or otherwise shaped to conform to a connector having a curved or otherwise non-planar profile.

FIG. 11A illustrates a first ribbon conductor 1100A in accordance with the present disclosure. The ribbon conductor 1100A includes a forked terminal end 1102A including each of a first segment 1104A and a second segment 1105A that curve and join at a common segment 1106A. The first segment 1104A and the second segment 1105A extend substantially parallel to each other and the common segment 1106A. Welding of the ribbon conductor 1100A to an underlying connector, such as a ring connector, may be accomplished by first and second welding electrodes on the first and second segments 1104A, 1105A. For example, as indicated in FIG. 11A, the first and second electrodes may be placed at a first weld location 1110A and a second weld location 1112A, respectively.

FIG. 11B illustrates a second ribbon conductor 1100B in accordance with the present disclosure. The ribbon conductor 1100B includes a u-shaped terminal end 1102B including each of a first segment 1104B and a second segment 1105B. More specifically, the first segment 1104B extends in a first direction that then curves such that the second segment 1105B extends in a second direction, opposite the first direction. FIG. 11B further includes example welding locations 1110B, 1112B on the first segment 1104B and the second segment 1105B, respectively.

FIG. 11C illustrates a third ribbon conductor 1100C in accordance with the present disclosure. The ribbon conductor 1100C includes a forked terminal end 1102C including each of a first segment 1104C and a second segment 1105C. The first segment 1104C and the second segment 1105C join at a common segment 1106C. More specifically, the first segment 1104C extends collinearly from the common segment 1106C, while the second segment 1105C is formed as an offshoot from the common segment 1106C that curves to extend parallel to the first segment 1104C. FIG. 11C further includes example welding locations 1110C, 1112C on the first segment 1104C and the second segment 1105C, respectively.

FIG. 11D illustrates a fourth ribbon conductor 1100D in accordance with the present disclosure. The ribbon conductor 1100D includes a forked terminal end 1102D including each of a first segment 1104D and a second segment 1105D. The forked terminal end 1102D of FIG. 11D is offset from a common segment 1106D by a curved connecting segment 1107D. FIG. 11D further includes example welding locations 1110D, 1112D on the first segment 1104D and the second segment 1105D, respectively.

Figure 11E:
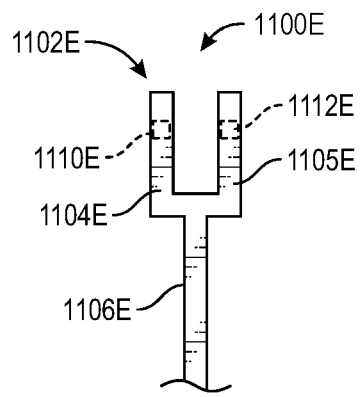

FIG. 11E illustrates a fifth ribbon conductor 1100E in accordance with the present disclosure. The ribbon conductor 1100E includes a forked terminal end 1102E including each of a first segment 1104E and a second segment 1105E that join at a common segment 1106E. The first segment 1104E and the second segment 1105E extend substantially parallel to each other and the common segment 1106E. In contrast to the curved fork shape of FIG. 11A, the forked terminal end 1102E is substantially square. FIG. 11E further includes example welding locations 1110E, 1112E on the first segment 1104E and the second segment 1105E, respectively.

Figure 11F:
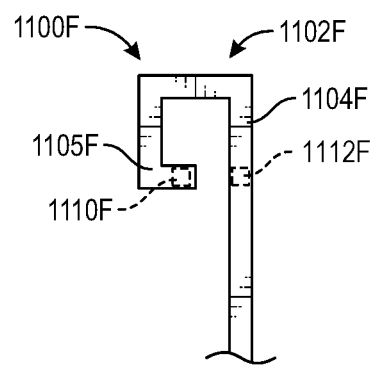

FIG. 11F illustrates a sixth ribbon conductor 1100F in accordance with the present disclosure. The ribbon conductor 1100F includes a terminal end 1102F including each of a first segment 1104F and a second segment 1105F. More specifically, the first segment 1104F extends in a first direction that then forms a squared spiral structure terminating in the second segment 1105F. FIG. 11F further includes example welding locations 1110F, 1112F on the first segment 1104F and the second segment 1105F, respectively.

Figure 11G:
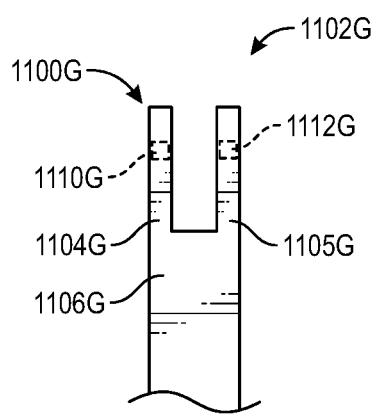

FIG. 11G illustrates a seventh ribbon conductor 1100G in accordance with the present disclosure. The ribbon conductor 1100G includes a forked terminal end 1102G including each of a first segment 1104G and a second segment 1105G which are joined at a common segment 1106G. In contrast to the preceding examples, the common segment 1106G has a substantially wider width than each of the first segment 1104G and the second segment 1105G, which may generally increase the strength and durability of the ribbon conductor 1100G. FIG. 11G further includes example welding locations 1110G, 1112G on the first segment 1104G and the second segment 1105G, respectively.

Figure 12:
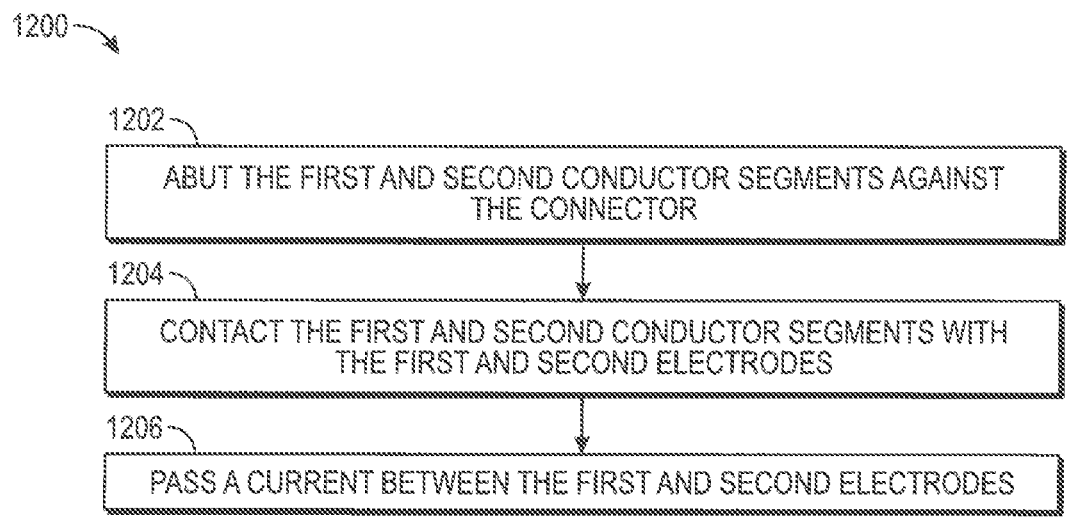
FIG. 12 is a flow chart illustrating a method of manufacturing an implantable electronic, device including a header connector assembly.

FIG. 12 is a flow chart illustrating a method 1200 of manufacturing an implantable electronic device including a header connector assembly. The method 1200 is particularly directed to coupling a conductor to a connector of the connector assembly. In certain implementations, the conductor may then be coupled to a feedthru or similar electrical component to communicate electrical signals from the implantable lead received through the connector to components within a housing of the implantable electronic device.

At operation 1202, first and second segments of the conductor are abutted against the connector. Generally, the first and second conductor segments are offset from each other. Various non-limiting examples of ribbon conductors having such segments are illustrated by the ribbon conductors 1100A-1100G of FIGS. 11A-11G. In certain, the connector may be a ring connector or similar connector having a curved surface. In such implementations, abutting the first and second conductor segments against the connector may include conforming each of the first and second conductor segments to the curved surface. Alternatively, the first and second conductor segments may be preformed to conform to the curved surface.

At operation 1204, a first electrode and a second electrode are made to contact the first conductor segment and the second conductor segment, respectively.

In implementations in which the first and second conductor segments combine at a common conductor segment, the first electrode and the second electrode may be positioned on the first and second conductor segments to minimize or eliminate shunting of current to the common segment. To do so, the first and second electrode may be placed on the first and second conductor segments such that the electrodes are disposed a distance from the junction of the first and second conductor segments that is equal to or greater than the width of the common segment.

At operation 1206, a current is passed between the first and second electrodes. The current then couples the first and second conductor segments to the connector through a resistance welding process. More specifically, the current generates heat at the interface between the first and second conductor segments and the connector that forms a melt pool. When cooled, the melt pool solidifies to bond the first and second conductor segments to the connector.

The foregoing merely illustrates the principles of the various embodiments described in this disclosure. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the disclosure and are thus within the spirit and scope of the present disclosure. From the above description and drawings, it will be understood by those of ordinary skill in the art that the particular embodiments shown and described are for purposes of illustrations only and are not intended to limit the scope of the present disclosure. References to details of particular embodiments are not intended to limit the scope of the disclosure.

What is claimed is:

1. An implantable electronic device comprising:
a housing;
a feedthru extending through the housing; and
a header connector assembly coupled to the housing, the header assembly comprising:
a connector assembly comprising a ring connector, the ring connector adapted to receive and electrically couple to a proximal lead end of an implantable medical lead; and
a conductor coupling the ring connector to the feedthru, the conductor comprising a first conductor segment and a second conductor segment offset from the first conductor segment,
wherein:
the first conductor segment is mechanically and electrically coupled to a first location of the ring connector by a first resistance weld joint, and
the second conductor segment is mechanically and electrically coupled to a second location of the ring connector by a second resistance weld joint.

2. The implantable electronic device of claim 1, wherein each of the first conductor segment and the second conductor segment are curved to conform to a profile of the ring connector.

3. The implantable electronic device of claim 1, wherein the first conductor segment and the second conductor segment are substantially flat.

4. The implantable electronic device of claim 1, wherein the conductor is formed from titanium and has a thickness from and including 0.003 inches to and including 0.050 inches.

5. The implantable electronic device of claim 1, wherein the conductor comprises a forked terminal portion including the first conductor segment and the second conductor segment such that the first conductor segment and the second conductor segment extend parallel to each other.

6. The implantable electronic device of claim 1, wherein the conductor comprises a common segment, the first conductor segment and the second conductor forming a junction at the common segment.

7. The implantable electronic device of claim 6, wherein the common segment has a common segment width, and each of the first location and the second location are disposed at a respective distance from the junction that is greater than or equal to the common segment width.

8. The implantable electronic device of claim 6, wherein the first conductor segment is aligned with the common segment and the second conductor segment extends from an offshoot of the common segment and extends parallel to the first conductor segment.

9. The implantable electronic device of claim 1, wherein the conductor is one of a ribbon conductor, a plate, and a wire.

10. The implantable electronic device of claim 1, wherein the first conductor segment has a first resistance and the second conductor segment has a second resistance substantially equal to the first resistance.

11. An implantable electronic device comprising:
a ring connector adapted to receive a lead end; and
a conductor coupled to the ring connector, the conductor comprising a first conductor segment and a second conductor segment offset from the first conductor segment,
wherein:
the first conductor segment is mechanically and electrically coupled to a first location of the ring connector by a first resistance weld joint, and
the second conductor segment is mechanically and electrically coupled to a second location of the ring connector by a second resistance weld joint.

12. The implantable electronic device of claim 11, wherein the conductor comprises a forked terminal portion including the first conductor segment and the second conductor segment such that the first conductor segment and the second conductor segment extend parallel to each other.

13. The implantable electronic device of claim 11, wherein the conductor is one of a ribbon conductor, a plate, and a wire.

14. The implantable electronic device of claim 11, wherein the first conductor segment has a first resistance and the second conductor segment has a second resistance substantially equal to the first resistance.

15. The implantable electronic device of claim 11, wherein the conductor is formed from titanium and has a thickness from and including 0.003 inches to and including 0.050 inches.

16. A method of manufacturing an implantable electronic device including a header connector assembly adapted to receive a proximal lead end of an implantable medical lead, the header connector assembly including a connector assembly including a ring connector, the method comprising:
abutting a conductor against the ring connector, wherein abutting the conductor against the ring connector includes abutting a first conductor segment against a first location of the ring connector and abutting a second conductor segment against a second location of the ring connector, the second location offset from the first location;
contacting the first conductor segment with a first electrode and the second conductor segment with a second electrode; and
resistance welding each of the first conductor segment and the second conductor segment to the ring connector by passing a current between the first electrode and the second electrode such that the first conductor segment and the second conductor segment are welded to the ring connector at respective joints.

17. The method of claim 16, further comprising conforming each of the first conductor segment and the second conductor segment to a curved surface of the ring connector.

18. The method of claim 16, wherein:
the first conductor segment and the second conductor segment form a junction at a common conductor segment having a common segment width, and
each of the first location and the second location are disposed at a respective distance from the junction that is greater than or equal to the common segment width.

* * * * *